(12) United States Patent
Hsieh et al.

(10) Patent No.: US 8,155,729 B1
(45) Date of Patent: Apr. 10, 2012

(54) METHOD AND APPARATUS TO COMPENSATE IMAGING DATA WITH SIMULTANEOUSLY ACQUIRED MOTION DATA

(75) Inventors: Jiang Hsieh, Brookfield, WI (US); Michael John Barber, Mequon, WI (US); Brian J. Kost, Waukesha, WI (US); William R. Clarke, Colgate, WI (US); Michael A. Juhl, Waukesha, WI (US); Anne Lindsay Hall, New Berlin, WI (US)

(73) Assignee: General Electric Company, Schenectady, NY (US)

( * ) Notice: Subject to any disclaimer, the term of this patent is extended or adjusted under 35 U.S.C. 154(b) by 1623 days.

(21) Appl. No.: 11/276,195

(22) Filed: Feb. 17, 2006

(51) Int. Cl.
*A61B 5/05* (2006.01)

(52) U.S. Cl. ........ 600/427; 600/410; 600/411; 600/425; 600/437; 600/439

(58) Field of Classification Search .................. 600/407, 600/410–411, 413, 425, 427–428, 437, 439
See application file for complete search history.

(56) References Cited

U.S. PATENT DOCUMENTS

| | | | | |
|---|---|---|---|---|
| 5,553,618 A * | 9/1996 | Suzuki et al. | ................. | 600/411 |
| 6,379,302 B1 * | 4/2002 | Kessman et al. | ............. | 600/437 |
| 6,505,063 B2 * | 1/2003 | Van Den Brink et al. | .... | 600/411 |
| 6,943,033 B2 * | 9/2005 | Van Zijl et al. | ............... | 436/173 |
| 7,127,025 B2 | 10/2006 | Bruder et al. | | |
| 2003/0195413 A1 * | 10/2003 | Rubin et al. | .................. | 600/411 |
| 2004/0147840 A1 * | 7/2004 | Duggirala et al. | ............ | 600/437 |
| 2006/0036167 A1 * | 2/2006 | Shina | ............................ | 600/433 |

FOREIGN PATENT DOCUMENTS

| CN | 1593689 A | 3/2005 |
|---|---|---|
| WO | WO2006015296 A2 | 2/2006 |

OTHER PUBLICATIONS

Eric Barnes, Echo May be More Accurate than ECG for Triggering Cardiac Scans, AuntMinnie.com, Dec. 6, 2005.

* cited by examiner

*Primary Examiner* — Tse Chen
*Assistant Examiner* — Peter Luong
(74) *Attorney, Agent, or Firm* — Ziolkowski Patent Solutions Group, SC (57) ABSTRACT

Motion data is acquired simultaneously and in real-time with image data. The motion data provides accurate and near-instant information as to the state and position of an object prone to motion. The present invention is particularly applicable for cardiac CT or MR imaging and other physiologically gated acquisitions. In the context of cardiac imaging, the motion data includes information regarding size and location of the heart during the cardiac phases (diastole, systole, etc.) during each cardiac cycle.

37 Claims, 5 Drawing Sheets

METHOD AND APPARATUS TO COMPENSATE IMAGING DATA WITH SIMULTANEOUSLY ACQUIRED MOTION DATA

BACKGROUND OF THE INVENTION

The present invention relates generally to diagnostic imaging and, more particularly, to a method and apparatus capable of correcting motion errors in imaging data acquired from an object prone to motion. This motion correction is advantageously achieved by using mechanical motion data acquired from the object with one modality coincident with imaging data acquisition from the object with another and different modality.

Various imaging modalities are often used to image objects in or prone to motion, such as the heart in cardiac studies. For example, in cardiac computed tomography (CT), magnetic resonance imaging (MRI) and other imaging modalities directed to the acquisition of data from an object prone to motion, one or more motion correction techniques are generally used to reduce motion-induced artifacts in the reconstructed images. In known studies, this motion correction or compensation can add significant complexity in post processing of the images.

In one specific example, CT imaging requires more than 180 degrees of projections to formulate an image. Because of various limitations in conventional CT scanners, the time necessary to collect a complete set of projections is significant relative to object motion. For example, cardiac CT imaging is typically performed with the aid of an electrocardiogram (EKG) signal which is used to synchronize data acquisition and image reconstruction with the phase of cardiac motion. The EKG signal collected from the patient represents the electrical properties of the heart and is helpful in identifying the quiescent period of cardiac activity, which is preferred for data acquisition. Moreover, the EKG signal assists in identifying this quiescent period over several cardiac cycles. By synchronizing data collection with the quiescent period of the cardiac cycle, image artifacts and spatial resolution due to heart motion are reduced. Additionally, by consistently identifying this quiescent period in successive cardiac cycles, inconsistency between images acquired at different cardiac cycles is reduced. EKG signals can be used similarly in MR and other imaging modalities.

Although this EKG gating performs satisfactorily in most cases, there is room for improvement. Specifically, conventional EKG gating does not provide mechanical motion detection. While an EKG signal can indicate that motion is occurring or is about to occur, it cannot provide accurate real-time placement data of the heart. This is primarily a function of EKG's measuring the electrical activity of the heart and inferring mechanical motion from this electrical activity. As it is the actual mechanical motion of the heart that contributes to sub-optimal image quality, cardiac images that depend on EKG signals either require significant post processing to correct for motion artifacts or require a very high slice acquisition rate.

That is, CT reconstruction does not have a priori information on heart motion. In conventional EKG gated cardiac CT studies, the heart is presumed to be a stationary object during most of the short acquisition period identified as the quiescent period in the acquired EKG signal. Conventionally, half-scan weighting is used to suppress the impact of motion; however, its effectiveness is less than optimal since half-scan weighting reduces the contribution of CT data acquired at both ends near the 180 degree projection angular range. The amount of data to be suppressed at both ends of the dataset remains constant and therefore does not change based on each data acquisition, since there is no a priori information available. However, the amount of data to be suppressed should change based on the motion characteristics of the scanned object. For data collected roughly in the center of the 180 degree projection angular range, the data is treated in an identical manner without any weighting. Further, even with a gantry speed of 0.3 s/rotation, the central region of the projection range constitutes a 150 ms temporal window, which is prohibitively slow to completely "freeze" cardiac motion. The data acquisition window for CT systems having dual tube-detector assemblies is still between 70-80 ms which is not sufficient to eliminate heart motion. It is generally recognized that 10-15 ms temporal resolution is necessary to acquire a motion-free dataset.

It would therefore be desirable to design an apparatus and method of acquiring mechanical motion data, rather than inferring mechanical motion data, for physiologically gating CT and other image modality acquisitions to acquire motion-free datasets. It would also be desirable to incorporate the mechanical motion data into the image reconstruction process to compensate for the motion. It would also be desirable to use elasticity and other information obtained from ultrasound to map to the CT images to provide additional functional information, such as the viability of tissue. It would also be desirable to use ultrasound information to assist in identifying calcium in a CT scan and conversely use the CT anatomical information gathered in a CT scan to correct for noise in an ultrasound image. It would also be desirable to use the ultrasound tissue Doppler mode to acquire the velocity map to characterize the wall motion and map it to the CT images to provide functional information.

BRIEF DESCRIPTION OF THE INVENTION

The present invention is directed to a method and apparatus for simultaneously acquiring imaging data with real-time motion data from an object prone to motion, and using the motion data for motion compensation in the imaging data.

Motion data is acquired simultaneously and in real-time with image data. The motion data is acquired with a scanner of one modality and provides accurate and near-instant information as to the state and position of an object prone to motion. The image data is acquired with a scanner of a different modality than that used to acquire the motion data. In this regard, the present invention is particularly applicable for cardiac CT and MR imaging and other physiologically gated acquisitions. It is also advantageous to overcome peristaltic motion of the patient. In the context of cardiac imaging, the mechanical motion data includes information regarding size, shape, and location of the heart during the cardiac phases (diastole, systole, etc.) during each cardiac cycle. Such detailed information is generally not attainable from EKG signals.

Therefore, in accordance with one aspect of the present invention, a combined modality imaging system is disclosed. The combined system includes an imaging device of a first modality constructed to obtain image data of a subject prone to motion. The combined system further includes a motion detection and characterization device of a second modality, different from the first modality, arranged and constructed to obtain motion data of the subject simultaneously with imaging device.

In accordance with another aspect of the invention, a method of diagnostic imaging is disclosed. The method includes the steps of acquiring imaging data as well as mechanical motion data from a subject. Moreover, the imaging data and mechanical motion data are acquired simultaneously.

In accordance with another aspect of the present invention, an imaging system is disclosed as comprising an ultrasound probe that acquires mechanical motion data from an object in motion over time as well as an imaging apparatus configured to acquire imaging data from the object. The object is disposed in an imaging volume having a plurality of voxels. A computer is programmed to determine a position of a selected voxel in the imaging volume as function of time from the mechanical motion data and determine a temporal window specific to the selected voxel for image reconstruction of the selected voxel. The computer then reconstructs an image of the selected voxel from imaging data acquired from the object in motion during the specific temporal window.

According to yet another aspect of the present invention, the invention is embodied in a computer readable storage medium having a computer program stored thereon that represents a set of instructions to be executed by a computer. The instructions cause the computer to calculate a mapping function that provides a location of each sub-volume of an imaging volume as a function of time from ultrasound data. The instructions further cause the computer to determine a respective acquisition window for each sub-volume of the imaging volume for the mapping function and reconstruct an image of the imaging volume substantially free of motion artifacts from imaging data acquired from the imaging volume.

In accordance with yet a further aspect, the invention is directed to a wearable ultrasound probe apparatus. The apparatus includes a wearable membrane as well as an ultrasound transducer that is integrated into the wearable membrane. The transducer is configured to maintain substantially consistent contact with a surface of an object to be imaged when the object has the wearable membrane disposed thereon.

In accordance with yet another aspect, the invention is directed to an ultrasound probe attached to or integrated with a patient table. In this regard, the invention allows for "hands-free" positioning of the ultrasound probe relative to the patient during data acquisition.

In accordance with yet another aspect, the invention includes an ultrasound probe operably connected to a positioning device that provides feedback regarding the orientation and/or position of the ultrasound probe. The orientation and/or position information may be recorded and used during image reconstruction to compensate for motion errors or other image artifacts.

According to a further aspect, the invention is embodied in a method wherein motion data and imaging data are simultaneously acquired. The motion and imaging data are acquired independently with different image modalities, e.g. ultrasound and CT, respectfully. The mechanical motion data may be used to correct for errors in the imaging data or, alternately, the motion data may be used to reduce noise in the imaging data.

Various other features and advantages of the present invention will be made apparent from the following detailed description and the drawings.

BRIEF DESCRIPTION OF THE DRAWINGS

The drawings illustrate one preferred embodiment presently contemplated for carrying out the invention.

In the drawings.

DETAILED DESCRIPTION OF THE PREFERRED EMBODIMENT

The present invention will be described with respect to a "third generation" CT scanner, but is equally applicable with other image modalities. Moreover, the present invention will be described with respect to an imaging system that includes a CT scanner that acquires image data and an ultrasound machine that acquires motion data from a patient. The CT scanner and ultrasound machine are stand-alone devices that can be used independently from one another, but, as will be described, can operate in tandem to acquire CT data and ultrasound data simultaneously. It is also contemplated that the present invention is applicable with an integrated CT/ultrasound system. It is further contemplated that the invention may be embodied in a combination ultrasound/MR system or a stand-alone ultrasound and a stand-alone MR scanner that work in tandem to acquire motion and image data.

Figure 1:
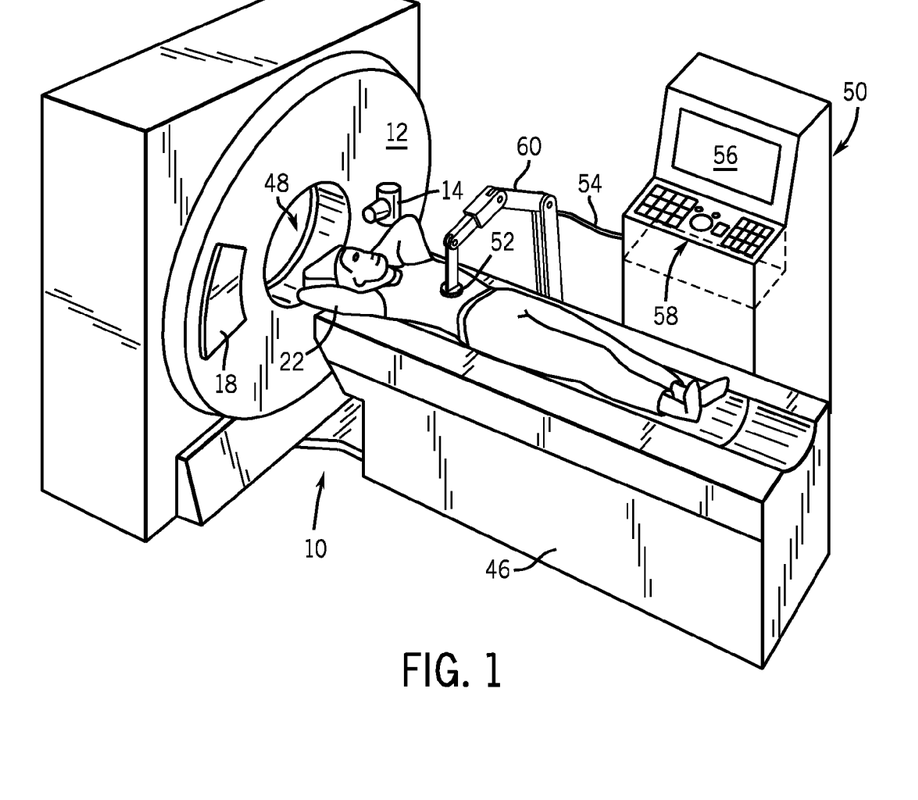
FIG. 1 is a pictorial perspective view of a CT imaging system.
Figure 2:
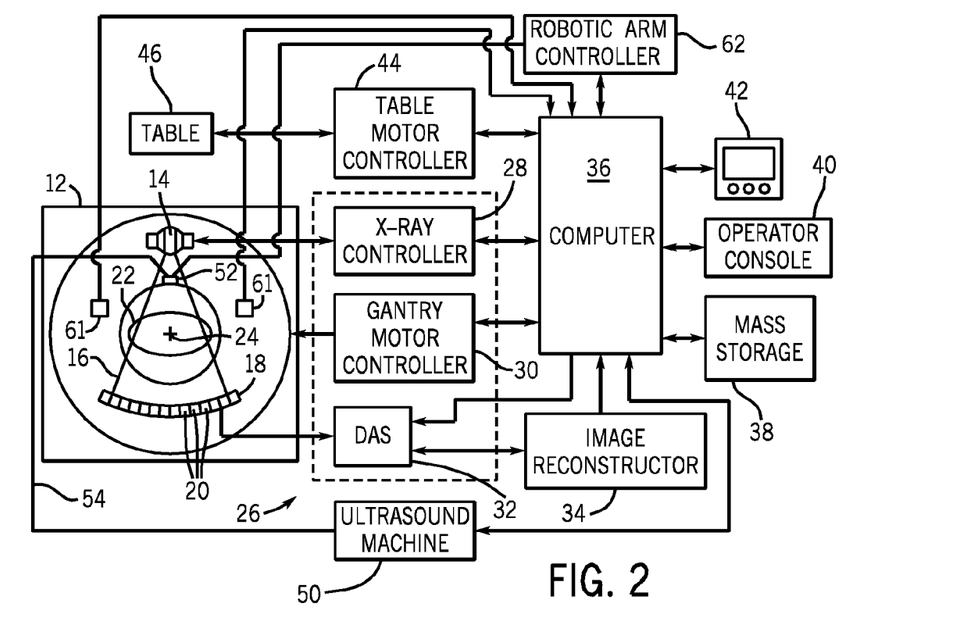
FIG. 2 is a block schematic diagram of the system illustrated in FIG. 1.

Referring to FIGS. 1 and 2, a computed tomography (CT) imaging system 10 is shown as including a gantry 12 representative of a "third generation" CT scanner. Gantry 12 has an x-ray source 14 that projects a beam of x-rays 16 toward a detector array 18 on the opposite side of the gantry 12. Detector array 18 is formed by a plurality of detectors 20 which together sense the projected x-rays that pass through a medical patient 22. Each detector 20 produces an electrical signal that represents the intensity of an impinging x-ray beam and hence the attenuated beam as it passes through the patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to an x-ray source 14 and a gantry motor controller 30 that controls the rotational speed and position of gantry 12. A data acquisition system (DAS) 32 in control mechanism 26 samples analog data from detectors 20 and converts the data to digital signals for subsequent processing. An image reconstructor 34 receives sampled and digitized x-ray data from DAS 32 and performs high speed reconstruction. The reconstructed image is applied as an input to a computer 36 which stores the image in a mass storage device 38.

Computer 36 also receives commands and scanning parameters from an operator via console 40 that has a keyboard. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table motor controller 44 which controls a motorized table 46 to position patient 22 and gantry 12. Particularly, table 46 moves portions of patient 22 through a gantry opening 48.

Still referring to FIGS. 1-2, in an exemplary embodiment, an ultrasound machine 50 having one or more ultrasound transducers 52 linked thereto by control and readout cable 54 is used to acquire mechanical motion data coincident with the acquisition of imaging data. The ultrasound machine includes a printer (not shown) for printing images displayed on monitor 56 as well as a keyboard and other input devices 58 to carry out an ultrasound study. In a preferred embodiment, the ultrasound machine is remotely positioned from the patient 22 and located at or near the operator console 40 of the CT scanner.

As will be described more fully below, the combined imaging system includes a robot arm 60 that controls positioning of the ultrasound transducer 52. The robot arm 60 is controlled by a robot arm controller 62 that is operably linked to the computer 36 or ultrasound machine 50.

The present invention is directed to a method and apparatus of simultaneously acquiring motion data of an object in motion and imaging data of that object. The mechanical motion data is used for motion correction or compensation of the imaging data. Preferably, the mechanical motion data is acquired with an ultrasound transducer. Ultrasound is preferred because it is a real-time imaging modality. Ultrasound provides accurate and near-instant information on the mechanical state of an object in motion, such as the heart. Since the ultrasound image depicts a cross-section of the object, rather than projection or integrated views, ultrasound imaging supplies sufficient information on object motion characteristics. For example, in the context of cardiac imaging, ultrasound can provide real-time information as to the size, shape, and location of the heart when it is in diastole, systole, or other phase of the cardiac cycle. As will be described, this advantage of ultrasound is exploited by simultaneously acquiring an ultrasound dataset and an imaging (such as CT) dataset, and using the ultrasound dataset for information on the shape and location of the heart to reduce motion induced artifacts in the imaging data set.

Figure 3:
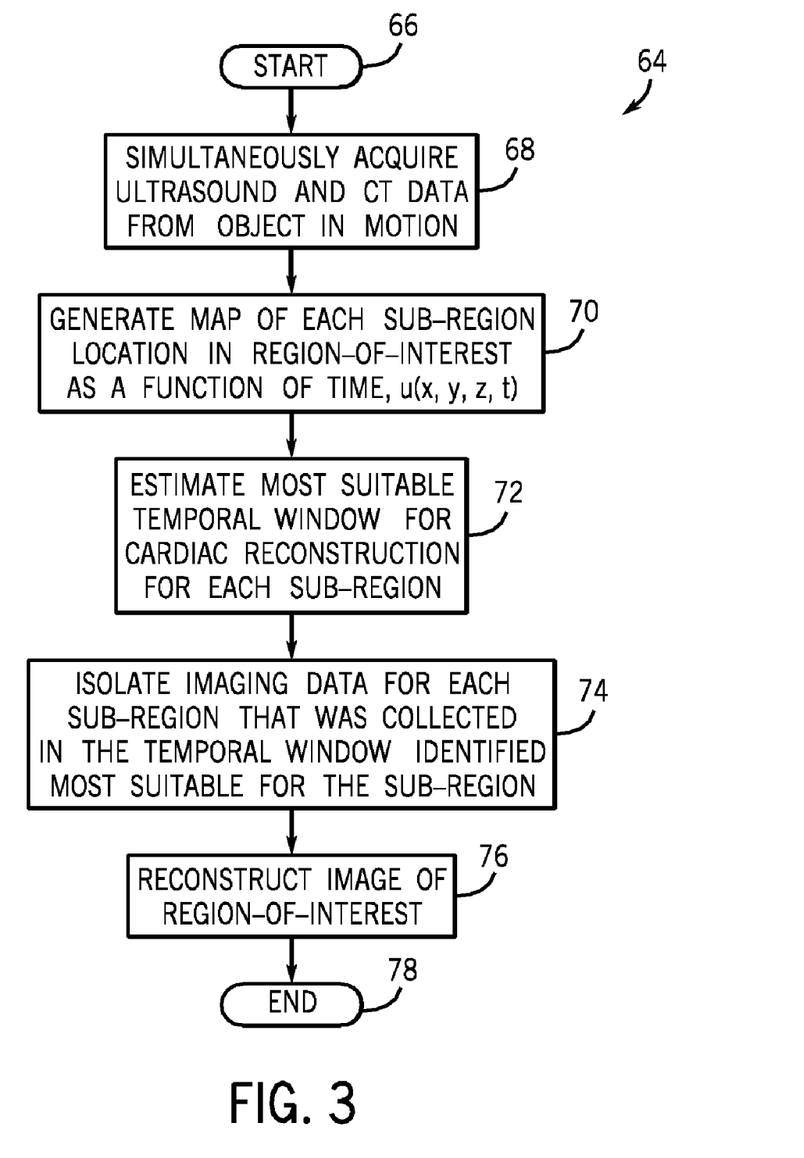
FIG. 3 is a flowchart setting forth the steps of a motion compensation technique according one aspect of the present invention.

Accordingly, referring now to FIG. 3, a flowchart setting forth steps of one exemplary technique for motion compensation is shown. The technique 64 begins at 66 with the simultaneous acquisition 68 of mechanical motion and imaging data from a volume of interest having an object experiencing motion therein. For purposes of illustration, the technique will be described with respect to the acquisition of the mechanical motion data of a heart using ultrasound and the acquisition of imaging data from the heart using CT.

The ultrasound data acquired at 68 provides near-instant information on the mechanical state of the heart. As such, cardiac motion of the heart under inspection is known from the ultrasound data. The technique then uses this knowledge of cardiac motion to generate a map that describes each voxel (sub-volume) of the heart volume as a function of time 70. Generally, the map can be characterized as a four dimensional function, u(x,y,z,t), where (x,y,z) represents the coordinate of a reconstructed voxel in the heart volume, and t represents time.

Since the map provides an indication of each voxel or sub-volume of the heart volume as a function of time, the optimal temporal window for reconstruction for each voxel may be readily determined 72. This is particularly advantageous for cardiac CT imaging as it is well-known that different portions of the heart move differently. For example, the optimal temporal window to effectively freeze motion in the right ventricle of the heart is different than the optimal temporal window to effectively freeze motion in the right coronary.

The cone-parallel geometry reconstruction algorithm can be described as:

$$f(x, y, z) = \int_0^{\Pi} \frac{R \cdot w(x, y, z, \beta)}{\sqrt{R^2 + Z^2}} \tilde{s}(\alpha, \beta, t) d\beta, \quad \text{(Eqn. 1)}$$

where:

$$\tilde{s}(\alpha,\beta,t) = s(\alpha,\beta,t) \otimes h(t) \quad \text{(Eqn. 2).}$$

Here, w(x, y, z, β) is a weighting function that controls the contribution of the projection to each voxel, and Π is the projection angular range required for reconstruction. One skilled in the art will appreciate that the weighting function shapes the temporal window for each voxel or sub-volume. In this regard, the technique effectively determines a temporal window best suited for freezing motion in the imaging volume on a per-voxel basis. As such, the technique isolates imaging data for each voxel 74 that falls within the temporal window determined for the voxel at 72. An image for the heart volume is then reconstructed in accordance with known reconstruction techniques at 76.

The reconstructed image is substantially free of motion artifacts as the ultrasound data acquired simultaneously with the imaging data has been used to effectively determine a temporal window on a per-voxel basis. In this regard, motion is effectively "frozen" in each voxel of the heart volume. By reconstructing an image wherein each voxel contains motion free data, the image, as a whole, will also be free of motion. Following image reconstruction, the technique ends at 78.

Figure 4:
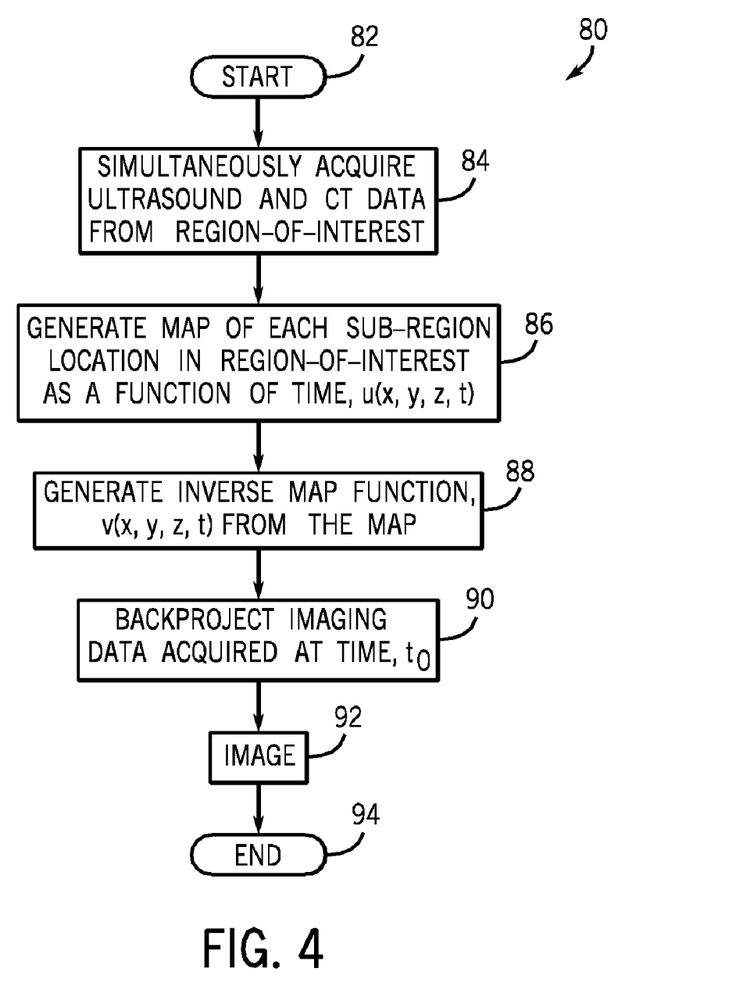
FIG. 4 is a flowchart setting forth the steps of a modified backprojection technique according to another aspect of the present invention.

Referring now to FIG. 4, the information garnered from the mapping function, u(x,y,z,t), may be used in the backprojection process to correct for errors caused by cardiac motion. It is contemplated that the technique of FIG. 4 may be carried out independently or in conjunction with the technique of FIG. 3. For purposes of illustration, the technique of FIG. 4 will be described independently. In this regard, technique 80 begins at 82 with the simultaneous acquisition of ultrasound and imaging data at 84. A 4D map that provides an indication of the coordinate transformation as a function of time for each voxel of the heart volume is generated at 86. The ultrasound information, as noted above, can then be used during backprojection to correct for motion errors.

To this end, an inverse mapping function, v(x,y,z,t), which translates each voxel at time t back to voxel location at a specific reference time $t_0$, is generated at 88. This inverse mapping supplements the cone beam backprojection process 90, as defined by the following expression:

$$f(x, y, z) = \int_0^{\Pi} w(x, y, z, \beta) \times v \left[ \frac{R}{\sqrt{R^2 + Z^2}} \tilde{s}(\alpha, \beta, t) \right] d\beta, \quad \text{(Eqn. 3)}$$

where:

$$\tilde{s}(\alpha,\beta,t) = s(\alpha,\beta,t) \otimes h(t) \quad \text{(Eqn. 4).}$$

It should be noted that the weighting function, w(x,y,z,β), in Eqn. 3 is different from the weighting function in Eqn. 1. The weighting function of Eqn. 3 represents a "confidence" weighting based on the degree of certainty that is placed on the belief that the inverse mapping function properly characterizes heart motion.

Still referring to FIG. 4, the backprojection process yields an image 92 whereupon the technique ends at 94. By taking advantage of the inverse map, the resulting image is a true image of the state of the heart at time $t_0$.

In addition to motion correction, the acquisition of complementary ultrasound and imaging data can also be used to assess the viability of tissues. That is, the ultrasound data can be used to generate an elasticity map. This elasticity map, in conjunction with the imaging data, can be used in conjunction with CT perfusion data to provide information regarding tissue viability. Specifically, the ultrasound and CT images can be fused together to provide a cardiac viability map. This is particularly advantageous in reducing radiation dose to a patient relative to conventional approaches in determining cardiac viability.

In conventional CT perfusion studies, the heart volume of a patient is scanned repeatedly to acquire functional information. This repeated data acquisition from the patient translates to significant levels of x-ray dose to the patient. However, with the present invention, because the ultrasound data is acquired coincident with the imaging data, the ultrasound data may be used to identify the viability of tissue. As a result, the customary repeated scans may be replaced by a single or a few scans, which yields a significant dose reduction. This dose reduction allows the single or few scans to be carried out at higher dose levels which increases SNR and CNR in the resulting images.

Moreover, the complimentary ultrasound and imaging data can be used to improve the detection and classification of plaques. Typically, several scans are required to classify a given plaque. The present invention reduces the need for such numerous scans, which provides a dose a reduction for such studies.

In a further embodiment of the invention, the complimentary ultrasound and imaging data is used for image noise reduction. Specifically, the ultrasound data provides additional boundary and anatomical information to supplement that gathered with CT. As such, during application of noise reduction algorithms, more information is known as to the structure of the tissue. In this regard, noise reduction can be carried out without impacting small anatomical structures that were identified with the ultrasound images but undetected or partially detected with CT.

The simultaneous acquisition of ultrasound and imaging data, i.e., CT data, is also effective in reducing "calcium blooming" and separating calcium from iodine or other marker. More particularly, the ultrasound images are used to further demarcate calcium from the iodine marker in the volume being imaged. Specifically, the ultrasound reflection of calcium is significantly different that the ultrasound reflection of iodine. As such, these reflection differences can be readily identified using ultrasound which aids in detecting the corresponding calcium deposits or plaques in the CT images.

Although the present invention has been described with respect to cardiac CT studies, one skilled in the art will appreciate that the present invention can be applied to correct other physiologically induced motion. For example, it is well known that CT images can be corrupted by the peristaltic motion of the patient. Conventional compensation techniques utilize a fixed weighting function to suppress contributions of the projection samples at both ends of the datasets. This approach has two shortcomings. The first is the increased noise and the second is the lack of effectiveness when the motion is large. With the ultrasound information, the weighting function can be modified based on the motion characteristics or the backprojection process can be changed to compensate for the motion. For example, when little motion is present, the weighting function can be nearly constant to minimize the noise. When the motion increases, the "underscan angle" can be increased accordingly to reduce the motion artifacts.

It is also understood that the motion compensation techniques described above, in the context of CT, can be used to reduce the requirements on acquisition speed. In conventional cardiac CT studies, the gantry rotation speed is typically 0.35 s per rotation. This places significant constraints on the mechanical, detector, and tube design. If the gantry speed can be reduced to 0.5 s while maintaining the same image quality, the CT system design can be simplified. Additionally, since the complimentary ultrasound data can be used to more fully characterize heart motion, the need for short scan times is reduced with the present invention. For example, it is recognized that the present invention enables heart studies to be conducted with a four-slice scanner that otherwise requires a 64-slice scanner, for example.

Figure 6:
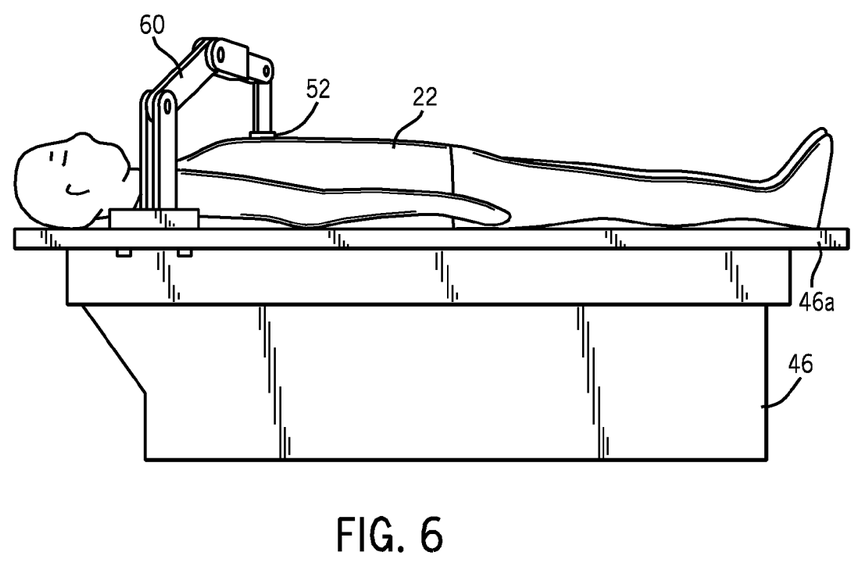
FIG. 6 is a side view of a movable patient table operably connected or integrated with an ultrasound transducer according to another aspect of the invention.

Referring back to FIGS. 1-2, in one embodiment to simultaneously acquire ultrasound and CT images without a technician moving the transducer, the ultrasound transducer 52 is robotically controlled by the robot arm 60. This allows for positioning of the transducer without operator presence in or near the imaging bore 48. In a preferred embodiment, the robot arm 65 is telescoping and therefore moves the transducer freely about the patient during data acquisition and/or during indexing of the patient through the bore. Preferably, the robot arm is controlled by the robot arm controller 62 that positions and controls the robot arm based on positioning controls manifested in user-inputs to the ultrasound machine 50 or, alternatively, the CT scanner operator console 40. It is also contemplated that the robotic arm may be automatically controlled based on user-inputs identifying those regions of the patient where it is desired to acquire ultrasound data. It also contemplated that a robotic arm may be controlled by a user making arm and hand movements that are sensed by a sensory array, and processed and transmitted as control commands to the robotic arm that cause the robotic arm to simulate the arm and hand movements of the user in near real-time. Alternatively, as shown in FIG. 6, the ultrasound probe can be integrated with the patient table 46(a) such that the probe 52 and patient 22 remain relatively stationary even when the patient 22 is indexed to different locations to scan different portions of the anatomy.

It is preferred that the ultrasound transducer and the robotic arm be fabricated so as to limit the metallic content thereof. By reducing the metallic content of the transducer or probe and the robotic arm, artifacts attributable to these devices in the reconstructed images are reduced. Furthermore, in one exemplary embodiment, the position of the ultrasound transducer is automatically determined and is used to register the acquired ultrasound images with the CT images. In this regard, it is contemplated that the ultrasound transducer may be included in a GPS network (not shown) that provides positional and orientation feedback to the ultrasound machine and/or CT scanner for image registration. It is also contemplated that various sensors, such as infrared sensors or laser positioning devices 61, FIG. 2, may be used to provide transducer position feedback to ultrasound machine 50 or CT computer 36.

Figure 5:
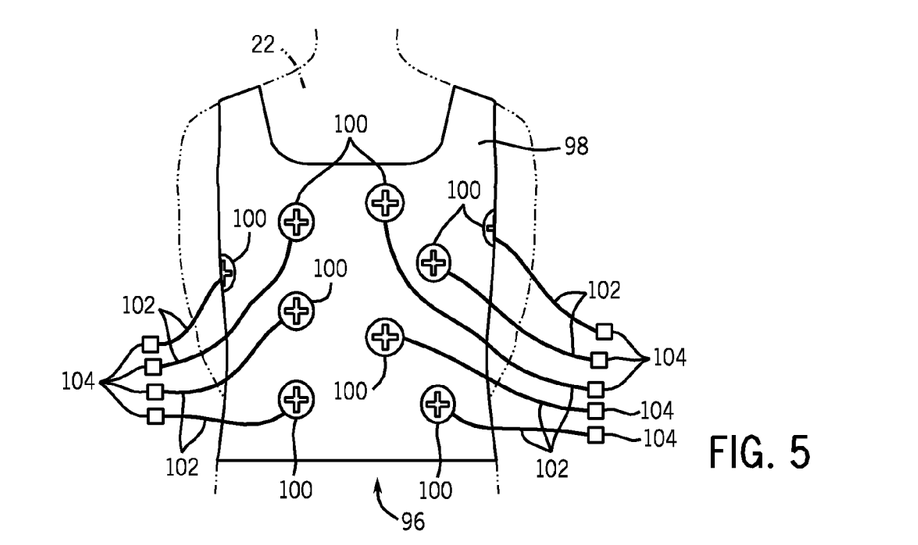
FIG. 5 is a pictorial view of a wearable ultrasound transducer apparatus according to an aspect of the present invention.

In an alternate embodiment, ultrasound data is acquired with a plurality of ultrasound transducers integrally formed with a wearable membrane, as illustrated in the wearable ultrasound probe assembly 96 shown in FIG. 5. The assembly 96 is constructed to allow imaging through the membrane and without appreciable noise in resulting images by a medical imaging scanner. As illustrated, the wearable membrane 98 includes ultrasound transducers 100 that are disposed about the wearable membrane 98. The wearable assembly is designed to be worn by a patient 22. In this regard, the wearable assembly 96 can be worn by the patient when the patient is not positioned on an imaging table. Each ultrasound transducer produces an ultrasonic beam and acquires ultrasound data from the patient. Each transducer has a readout lead 102 with a quick-connect jumper 104. The quick-connect jumpers 104 allow the assembly or jacket to be quickly connected/disconnected from the ultrasound machine. It is also contemplated that each readout lead may be routed through the wearable membrane to a common multi-pin port (not shown) so that a single cable (not shown) can be used to connect the transducers to the ultrasound machine.

It is contemplated that the transducers can be collectively or independently controlled. In this regard, it is contemplated that one transducer may be enabled for data collection whereas another transducer is disabled. It is contemplated that the wearable assembly may take the form of a vest, belt, wrap, or other article. In any event, it is preferred that the membrane be snuggly fit to the patient to ensure that the transducers are in contact with the skin of the patient. Accordingly, it is contemplated that the membrane may be formed of elastic material so that one size fits all or multiple sized membranes may be used to accommodate variations in patient population.

Preferably, the wearable membrane is formed of non-metallic material, such as fabric. It is also preferred the membrane being relatively comfortable for the patient. One skilled in the art will appreciate that the principles of the wearable assembly shown and described with respect to FIG. 5 may be adopted to be more appropriately shaped for other anatomical regions of the patient. It is also preferred that the wearable membrane include a sufficient number of transducers so that desired structures may be imaged without requiring repositioning of the membrane on the patient.

Therefore, in accordance with one embodiment of the present invention, a combined modality imaging system is disclosed. The combined system includes an imaging device of a first modality constructed to obtain image data of a subject prone to motion. The combined system further includes a motion detection/characterization device of a second modality, different from the first modality, arranged and constructed to obtain motion data of the subject simultaneously with the imaging device.

In accordance with a further embodiment, a method of diagnostic imaging is disclosed. The method includes the steps of acquiring imaging data as well as mechanical motion data from a subject. Moreover, the imaging data and mechanical motion data are acquired simultaneously. While the present invention has been described to using an ultrasound or similar imaging modality to acquire motion data, one skilled in the art will appreciated that an EKG system may also be used to acquire EKG signals can still be used to in conjuction with ultrasound data to further aid in the characterization of the motion. For example, the ultrasound probe and the EKG leads can be integrated together to provide both electrical as well as mechanical information.

In accordance with another embodiment of the present invention, an imaging system is disclosed as comprising an ultrasound probe that acquires mechanical motion data from an object in motion over time as well as an imaging apparatus configured to acquire imaging data from the object. The object is disposed in an imaging volume having a plurality of voxels. A computer is programmed to determine a position of a selected voxel in the imaging volume as function of time from the mechanical motion data and determine a temporal window specific to the selected voxel for image reconstruction of the selected voxel. The computer then reconstructs an image of the selected voxel from imaging data acquired from the object in motion during the specific temporal window.

According to yet another embodiment of the present invention, the invention is embodied in a computer readable storage medium having a computer program stored thereon that represents a set of instructions to be executed by a computer. The instructions cause the computer to calculate a mapping function that provides a location of each sub-volume of an imaging volume as a function of time from ultrasound data. The instructions further cause the computer to determine a respective acquisition window for each sub-volume of the imaging volume for the mapping function and reconstruct an image of the imaging volume substantially free of motion artifacts from imaging data acquired from the imaging volume.

In accordance with yet a further embodiment, the invention is directed to a wearable ultrasound probe apparatus. The apparatus includes a wearable membrane as well as an ultrasound transducer that is integrated into the wearable membrane. The transducer is configured to maintain substantially consistent contact with a surface of an object to be imaged when the object has the wearable membrane disposed thereon.

The invention is also directed to an ultrasound probe attached to or integrated with a patient table. In this regard, the invention allows for "hands-free" positioning of the ultrasound probe relative to the patient during data acquisition.

The invention also includes an ultrasound probe operably connected to a positioning device that provides feedback regarding the orientation and/or position of the ultrasound probe. The orientation and/or position information may be recorded and used during image reconstruction to compensate for motion errors or other image artifacts.

The invention is also embodied in a method wherein motion data and imaging data are simultaneously acquired. The motion and imaging data are acquired independently with different image modalities, e.g. ultrasound and CT, respectfully. The mechanical motion data may be used to correct for errors in the imaging data or, alternately, the motion data may be used to reduce noise in the imaging data.

The present invention has been described in terms of the preferred embodiment, and it is recognized that equivalents, alternatives, and modifications, aside from those expressly stated, are possible and within the scope of the appending claims.

What is claimed is:

1. A combined modality imaging system comprising:
an imaging device of a first modality constructed to obtain image data of a subject prone to motion;
a motion detection device of a second modality, different form the first modality, arranged and constructed to obtain motion data of the subject simultaneously with the imaging device; and
a computer readable storage medium having a computer program stored thereon and representing a set of instructions that when executed by a computer causes the computer to:
calculate a mapping function that provides a location of each sub-volume of an imaging volume as a function of time from ultrasound data;
determine a respective acquisition window for each sub-volume of the imaging volume from the mapping function; and reconstruct an image of the imaging volume substantially free of motion artifacts from imaging data acquired from the imaging volume during the respective acquisition window.

2. The combined modality imaging system of claim 1 wherein the first modality of the imaging device is one of CT, MR, optical, x-ray, and PET.

3. The combined modality imaging system of claim 1 wherein the second modality of the motion detection device is constructed for patient physiological gating.

4. The combined modality imaging system of claim 1 wherein the second modality of the motion detection device is ultrasound.

5. The combined modality imaging system of claim 4 wherein the motion detection device includes a patient wearable belt having an ultrasound transducer.

6. The combined modality imaging system of claim 4 wherein the motion detection device includes a 3D ultrasound probe mechanically connected about the patient and remotely steerable by a technician.

7. The combined modality imaging system of claim 4 further comprising a set of laser or infrared detection devices arranged to register an ultrasound probe location relative to a desired patient orientation.

8. The combined modality imaging system of claim 4 further comprising a robot arm connected to an ultrasound probe and configured to position the ultrasound probe during data acquisition.

9. The computer readable storage medium of claim 1 wherein the imaging data is acquired in a series of projections and wherein the computer is further programmed to calculate a weighting function that controls contribution of each projection to reconstruction of a sub-volume.

10. The computer readable storage medium of claim 1 wherein the computer is further programmed to apply the mapping function during cone beam backprojection of the imaging data.

11. The computer readable storage medium of claim 10 wherein the computer is further programmed to calculate an inverse mapping function that translates each sub-volume of the imaging volume at time t back to a sub-volume location at a specific reference time $t_0$.

12. A method of diagnostic imaging comprising the steps:
acquiring imaging data from a subject in one modality;
acquiring mechanical motion data from the subject in another modality, over time, from an imaging volume of the subject that is in motion, the imaging volume having a plurality of sub-volumes;
wherein the imaging data and mechanical motion data are acquired simultaneously from the subject;
mapping a location of each sub-volume of the imaging volume over time from the mechanical motion data;
for each sub-volume, determining a respective temporal window for image reconstruction thereof that results in freezing of motion therein based on the mapped locations;
reconstructing an image from imaging data acquired from the selected sub-volumes during the determined temporal windows.

13. The method of claim 12 wherein one modality is ultrasound and the another modality is one of a CT machine, an MR machine, a PET machine, and an x-ray machine.

14. The method of claim 12 wherein the selected sub-volume is a voxel of the imaging volume.

15. The method of claim 12 wherein the selected sub-volume is a selected anatomical structure in the imaging volume, the selected anatomical structure having motion different from at least one other sub-volume in the imaging volume.

16. The method of claim 12 further comprising the step of determining a temporal window for a sub-volume that effectively freezes motion in the sub-volume.

17. The method of claim 12 wherein the imaging data includes perfusion data, and further comprising the steps of generating an elasticity map from the mechanical motion data and fusing the elasticity map with the perfusion data to generate a tissue viability map.

18. The method of claim 12 wherein the imaging data includes anatomical data, and further comprising the steps of generating an elasticity map from the mechanical motion data and fusing the elasticity map with the anatomical data to generate a tissue viability map.

19. The method of claim 12 wherein the imaging data is fused with an ultrasound tissue Doppler map to generate a functional information map.

20. The method of claim 12 further comprising the steps of:
acquiring the mechanical motion data from the subject with a bolus traveling through an imaging volume thereof;
differentiating calcium from the bolus in the imaging volume from the reconstructed image; and
targeting CT calcification scoring of the calcium in the imaging volume differentiated from the bolus.

21. The method of claim 12 further comprising the step of steering an ultrasound transducer in real-time to acquire the mechanical motion data based on anatomical markers identified in an image reconstructed from acquired imaging data.

22. The method of claim 21 further comprising the step of determining a position of the ultrasound transducer and automatically registering acquired mechanical motion data with imaging data based at least one the position of the ultrasound transducer when acquiring the mechanical motion data.

23. The method of claim 22 further comprising the step of automatically determining the position of the ultrasound transducer.

24. The method of claim 21 wherein the ultrasound transducer is robotically controlled.

25. The method of claim 21 wherein the ultrasound transducer includes an array of transducer elements affixable to the subject and further comprising the step of selectively controlling each transducer element to generate an ultrasonic beam through the subject.

26. An imaging system comprising:
an ultrasound probe configured to acquire motion data from an object prone to motion over time, the object disposed in an imaging volume and having a volume comprising a plurality of sub-volumes;
an imaging apparatus configured to acquire imaging data from each of the sub-volumes of the object; and
a computer programmed to:
determine a position of each sub-volume of the plurality of sub-volumes in the imaging volume as a function of time from the mechanical motion data;
generate a mapping function from the determined positions, wherein the mapping function is a four dimensional function u(x, y, z, t) where (x, y, z) corresponds to a coordinate of a reconstructed sub-volume and t corresponds to time;
determine a plurality of temporal windows, wherein each temporal window is specific to a sub-volume of the plurality of sub-volumes;

for each sub-volume, determine an optimized temporal window from the mapping function based on an amount of mechanical motion in the sub-volume; and
reconstruct an image from imaging data acquired from each sub-volume during the optimized temporal windows.

27. The imaging system of claim 26 wherein the imaging apparatus is one of a CT machine, an MR machine, a PET machine, and an x-ray machine.

28. The imaging system of claim 26 wherein the computer is further programmed to determine the optimized temporal window for reconstruction of a given sub-volume that results in freezing of motion in the given sub-volume.

29. The imaging system of claim 28 wherein the imaging apparatus is further programmed to acquire the imaging data in a series of projections and wherein the computer is further programmed to determine a weighting function $w(x, y, z)$ that controls contribution of a given projection to reconstruction of a given sub-volume.

30. The imaging system of claim 26 wherein the computer is further programmed to use the mechanical motion data to correct for motion errors during backprojection of the imaging data.

31. The imaging system of claim 30 wherein the computer is further programmed to determine an inverse mapping function $v(x, y, z, t)$ that translates each sub-volume at time t back to a sub-volume location at a specific reference time $t_0$.

32. The imaging system of claim 31 wherein the computer is further programmed to reconstruct an image from the imaging data, the image representative of the imaging volume at time $t_0$.

33. The imaging system of claim 26 wherein the ultrasound probe and the imaging apparatus acquire data simultaneously.

34. The imaging system of claim 33 further comprising an ultrasound probe locating device that provides positional feedback regarding a location of the ultrasound probe.

35. The imaging system of claim 34 wherein the computer is further programmed to automatically register mechanical motion data with imaging data based at least on the location of the ultrasound probe during acquisition of the mechanical motion data.

36. The imaging system of claim 26 further comprising an operator interface that allows an operator to position the ultrasound probe for data acquisition without interference with imaging data acquisition.

37. A method of diagnostic imaging comprising the steps:
acquiring imaging data from a subject in one modality;
acquiring mechanical motion data from the subject in another modality;
wherein the imaging data and mechanical motion data are acquired simultaneously from the subject;
determining an inverse mapping function that translates each voxel of an imaging volume from which mechanical motion and imaging data are acquired at a given time to a voxel location at a specific reference time; and
reconstructing an image of the imaging volume representative of the imaging volume at the specific reference time.

* * * * *